United States Patent
Filosa et al.

(10) Patent No.: US 9,447,377 B2
(45) Date of Patent: Sep. 20, 2016

(54) ENDODERMAL CELLS FROM PLURIPOTENT CELLS

(75) Inventors: Stefania Filosa, Naples (IT); Genesia Manganelli, Avellino (IT)

(73) Assignee: Stefania Filosa, Portici (IT)

( * ) Notice: Subject to any disclaimer, the term of this patent is extended or adjusted under 35 U.S.C. 154(b) by 0 days.

(21) Appl. No.: 14/126,923

(22) PCT Filed: Jun. 15, 2012

(86) PCT No.: PCT/EP2012/061435
§ 371 (c)(1),
(2), (4) Date: Mar. 13, 2014

(87) PCT Pub. No.: WO2012/172045
PCT Pub. Date: Dec. 20, 2012

(65) Prior Publication Data
US 2014/0287504 A1    Sep. 25, 2014

(30) Foreign Application Priority Data
Jun. 17, 2011    (IT) ............... MI2011A1096

(51) Int. Cl.
| | | |
|---|---|---|
| *C12N 5/00* | (2006.01) | |
| *C12N 5/02* | (2006.01) | |
| *C12N 5/073* | (2010.01) | |
| *C12N 5/071* | (2010.01) | |
| *A61F 13/00* | (2006.01) | |

(52) U.S. Cl.
CPC ........... *C12N 5/0603* (2013.01); *C12N 5/0676* (2013.01); *C12N 5/0678* (2013.01); *C12N 2500/90* (2013.01); *C12N 2501/39* (2013.01); *C12N 2501/71* (2013.01); *C12N 2506/02* (2013.01); *C12N 2506/45* (2013.01); *C12N 2533/54* (2013.01)

(58) Field of Classification Search
CPC C12N 5/0603; C12N 5/0676; C12N 5/0678; C12N 2500/90; C12N 2506/02; C12N 2506/45

USPC .................................................. 435/377, 397
See application file for complete search history.

(56) References Cited

PUBLICATIONS

Paglialunga F et al. G6PD is indispensable for erythropoiesis after the embryonic-adult hemoglobin switch. Blood 104:3148-3152, 2004.*
Kubo A et al. Development of definitive endoderm from embryonic stem cells in culture. Development 131:1651-1662, 2004.*
Borowiak M et al. Small molecules efficiently direct endodermal differentiation of mouse and human embryonic stem cells. Cell Stem Cell 4:348-358, 2009.*
Bone, Heather, K., et al., "A Novel Chemically Directed Route for the Generation of Definitive Endoderm from Human Embryonic Stem Cells Based on Inhibition of GSK-3." Journal of Cell Science, Jun. 15, 2011, vol. 124, No. Pt. 12, pp. 1992-2000.
Touboul, Thomas, et al., "Generation of Functional Hepatocytes from Human Embryonic Stem Cells Under Chemically Defined Conditions that Recapitulate Liver Development," Hepatology, Baltimore MD, May 2010, vol. 51, No. 5, pp. 1754-1765.
Manganelli, Genesia. et al., "Modulation of The Pentose Phosphate Pathway Induces Endodermal Differentiation in Embryonic Stem Cells," PLOS One, vol. 7, No. 1, Jan. 12, 2012, p. E29321.
Livigni, Alessandra, et al., "Differentiation of Embryonic Stem Cells into Anterior Definitive Endoderm," Current Protocols in Stem Cell Biology, Jul. 2009, Chapter 1, Published online Jul. 2009 in Wiley Interscience (www.interscience.wiley.com). 10 pages.
Fico, Annalisa, et al., "High-Throughput Screening-Compatible Single-Step Protocol to Differentiate Embryonic Stem Cells in Neurons," Stem Cells and Development, vol. 17, No. 3, Jun. 2008. 573-584.

* cited by examiner

*Primary Examiner* — Quang Nguyen
(74) *Attorney, Agent, or Firm* — Thomas Horstemeyer, LLP

(57) ABSTRACT

The present inventions describes a method that, starting from pluripotent cells, leads to the obtainment, in a reproducible and efficient manner, of endodermal cells precursor. These cells reveal useful also for application in the regenerative therapy.

8 Claims, 2 Drawing Sheets

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Forward  primer

<400> SEQUENCE: 1
ggagggtcac cactgcttta                                              20

<210> SEQ ID NO 2
<211> LENGTH: 20
<212> TYPE: DNA
<213> ORGANISM: Artificial sequence
<220> FEATURE:
<223> OTHER INFORMATION: Reverse primer

<400> SEQUENCE: 2
agatgtctgg aggtgctgct                                              20

<210> SEQ ID NO 3
<211> LENGTH: 21
<212> TYPE: DNA
<213> ORGANISM: Artificial sequence
<220> FEATURE:
<223> OTHER INFORMATION: Forward primer

<400> SEQUENCE: 3
cactatgggc acagcagctc c                                            21

<210> SEQ ID NO 4
```

```
<211> LENGTH: 21
<212> TYPE: DNA
<213> ORGANISM: Artificial sequence
<220> FEATURE:
<223> OTHER INFORMATION: Reverse primer

<400> SEQUENCE: 4
ttggagctgg cctgcgatgt c                                              21

<210> SEQ ID NO 5
<211> LENGTH: 20
<212> TYPE: DNA
<213> ORGANISM: Artificial sequence
<220> FEATURE:
<223> OTHER INFORMATION: Forward primer

<400> SEQUENCE: 5
tcttctgggt ggcagtgatg                                                20

<210> SEQ ID NO 6
<211> LENGTH: 20
<212> TYPE: DNA
<213> ORGANISM: Artificial sequence
<220> FEATURE:
<223> OTHER INFORMATION: Reverse primer

<400> SEQUENCE: 6
tgcaccacca actgcttagc                                                20

<210> SEQ ID NO 7
<211> LENGTH: 20
<212> TYPE: DNA
<213> ORGANISM: Artificial sequence
<220> FEATURE:
<223> OTHER INFORMATION: Forward primer

<400> SEQUENCE: 7
tcacgcgtgg aaaggccagt                                                20

<210> SEQ ID NO 8
<211> LENGTH: 20
<212> TYPE: DNA
<213> ORGANISM: Artificial sequence
<220> FEATURE:
<223> OTHER INFORMATION: Reverse primer

<400> SEQUENCE: 8
gtgtaggcag tacgggtcct                                                20
```

ENDODERMAL CELLS FROM PLURIPOTENT CELLS

CROSS-REFERENCE TO RELATED APPLICATION

This application is the 35 U.S.C. §371 national stage of PCT application PCT/EP2012/061435, filed Jun. 15, 2012 which claims priority to Italian Patent Application No. MI2011A001096, dated Jun. 17, 2011, both of which are incorporated by reference in their entirety.

SEQUENCE LISTING

This application contains a sequence listing filed in electronic form as an ASCII.txt file entitled 01988403.txt, created on Mar. 13, 2014, and having a size of 1,671 bytes. The content of the sequence listing is incorporated herein in its entirety.

The present invention discloses a method which, starting from pluripotent cells, leads to the achievement, in a reproducible and effective manner, of endodermal precursor cells, which can be used also in regenerative therapy.

BACKGROUND OF THE ART

Cystic fibrosis, hepatitis, and diabetes are diseases that afflict over 150 million people worldwide. The three above-mentioned diseases have in common that they affect organs derived from the endoderm, one of the three primary layers of cells that compose the human embryo on the tenth day of life, and from which the different body tissues will subsequently develop. In particular, from the endoderm, there will be the generation of: the digestive tract, the respiratory tract, the bladder, part of the urethra and vagina, the middle ear, the mucosa overlying liver and pancreas, the thyroid, the parathyroid glands, and the remaining endocrine glands, the mucosa covering the digestive and respiratory systems.

There are many diseases involving organs derived from the endoderm; for those mentioned above, the current therapies based on organ transplantation are clearly limited by the availability of tissues derived from donors.

An alternative to the organ transplantation is offered by the huge potentialities resulting from the increasingly detailed knowledge of the stem cells, undifferentiated pluripotent cells that proliferate indefinitely and are able to differentiate, potentially giving rise to all the cell types in the body. The pluripotent cells are the embryo cells before the formation of the three germ layers. Said pluripotent stem cells are typically isolated from the inner cell mass of the embryo, at the so-called blastocyst stage. These cells are therefore called embryonic stem cells. An alternative source of pluripotent cells is offered by iPS (induced Pluripotent Stem) cells, which are reprogrammed adult cells and having characteristics similar to the cells that are generated in the embryo, described in JP20050359537.

A crucial step for the achievement of the expected applicative implications of pluripotent cells is to provide methods which allow, in a reproducible way, to induce the differentiation towards the desired cell type. In fact, the application in the regenerative therapy of pluripotent cells becomes a reality when, from said inexhaustible source of cells, it becomes possible to derive precisely the desired cell type. The differentiation must necessarily take place in a homogeneous manner, since the organ replacement is feasible only if the available cell population is composed exclusively of the proper cell type.

In recent years, research made considerable efforts to produce endodermal precursor cells, but the results obtained to date are modest. Among the methods proposed to induce the differentiation of pluripotent cells towards endodermal precursor cells, some authors propose the differentiation through an embryo bodies (EBs) differentiation stage in culture. Through a serum exposure, or due to an exposure to activin A in the absence of serum, the endoderm induction starting from EBs has been shown (Kubo A et al., Development 2004). The critical aspects in said method must necessarily be overcome from a therapeutic point of view. EBs are aggregates of cells derived from embryonic stem cells. Said cells are forced to aggregate by preventing the adhesion thereof to the culture dish bottom. The thus-aggregated cells begin a differentiation process that somewhat reflects the embryonic development. The obtained differentiation, despite the same happens in a three-dimensional structure, however, is very disorganized when compared to the physiological embryonic development, and the formed three-dimensional structure prevents to highlight and identify all the cells composing it, leading to non-selected cultures in the cell types that compose them. Furthermore, importantly, the three-dimensional structure prevents a uniform exposure of the cells to the factors that are present in the culture medium, and, prospectively, it features greater difficulties when it must be implemented so as to be applicable to large scale processes. Furthermore, the expected serum exposure is to be avoided absolutely from the therapeutic point of view, because the serum is a medium, the chemical composition of which is not necessarily completely defined; furthermore, it is of animal origin, generally bovine origin, thus it can lead to the onset of incompatibility phenomena when cells exposed thereto are transferred into a human being.

A further method for the differentiation towards endoderm is proposed by Kim et al. (Kim PTW et al., PLOS ONE 2010). The authors proceed with the differentiation of embryonic stem cells without the transition to EBs and by using all-trans retinoic acid and dibutyryl cAMP. While overcoming the problems associated to EBs, also in this case there remains the presence of fetal bovine serum in the culture medium.

The induction of endodermal cells starting from ES cells by the use of small molecules capable of crossing the cell membrane is described in Borowiak M et al., Cell Stem Cell 2009. The authors, from a screening of 4,000 molecules, select two molecules which are able to promote the differentiation towards endoderm. The two molecules, so-called IDE1 and IDE2, 2-[(6-carboxy-hexanoyl)-hydrazonomethyl]-benzoic acid and 7-(2-cyclopentylidenehydrazino)-7-oxoheptanoic acid, are putative inhibitors of the histone deacetylase enzymes. In this case also, the culture medium used for the maintenance in culture and the differentiation of ES cells comprises fetal bovine serum.

The object of the present invention is to provide a method which allows obtaining, in an efficient and reproducible manner, and without using components which are not chemically defined in the culture medium, a culture highly enriched with endodermal precursor cells, which cells will be able to find application in the regenerative therapy aimed at diseases involving organs of endodermal derivation.

DESCRIPTION OF THE INVENTION

The present invention discloses a method which, starting from pluripotent cells, leads to the achievement, in a reproducible and efficient manner, of endodermal precursor cells.

Said method is applicable on a large scale, and it meets the requirements that are necessary in order to be implemented on cells, which can be used in the regenerative therapy in humans and animals.

In the present description, by the term "pluripotent cells" is meant a cell population capable of giving rise, if suitably stimulated, to individual tissues and to any cell type constituting the body. These pluripotent cells are not capable of giving rise to extraembryonic tissues.

Said pluripotent cells can be obtained from the inner cell mass, i.e., from the cells within the blastocyst, which is a structure that forms in a very early stage of the embryonic development. Alternatively, said pluripotent cells are induced pluripotent stem cells, commonly abbreviated as iPS. These cells are pluripotent stem cells that are artificially derived from a non-pluripotent cell, typically an adult somatic cell.

The pentose phosphate pathway (PPP) is a cytoplasmic anabolic pathway that uses the 6 carbons present in the glucose molecule to generate sugars with 5 carbon atoms and NADPH. It is distinguished in a first oxidative phase, which consists in the generation of 2 NADPH molecules and one ribulose-5-P molecule, and in a second non-oxidative phase, which exhibits the reconversion into hexose sugars of the generated pentose sugars, which reconversion is mediated by the enzymes transketolase and transaldolase. The main enzyme in the pathway, which intervenes in the first phase, is the glucose 6-phosphate dehydrogenase (G6PD). The main purposes of said pathway are the provision of precursors for the synthesis of nucleotides and the production of molecules having a reducing power, thus contributing to the prevention of the oxidative stress. The pathway operates in all cells, but the highest levels of PPP enzymes (particularly, G6PD) are observed in neutrophils and macrophages.

Surprisingly, it has been observed herein that the PPP pathway inhibition in pluripotent cells is capable of directing in a specific and efficient manner the differentiation thereof towards endodermal-type precursors.

DETAILED DESCRIPTION OF THE INVENTION

Figure 1A:
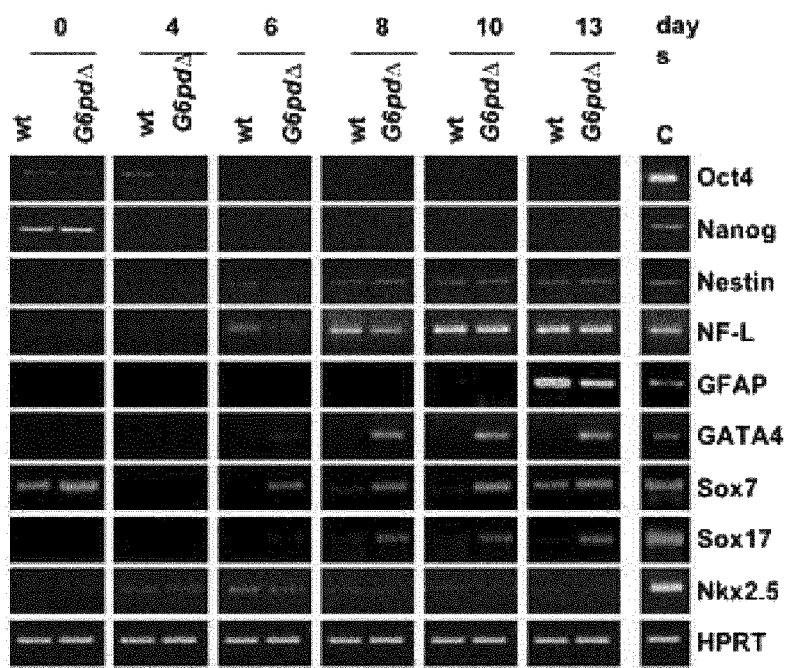
FIG. 1: (A) RT-PCR analysis of different markers in wt and G6pdΔ cells during the neural differentiation. The C line, a positive control, is represented by RNA isolated from embryos on day 14. Amplified HPRT is shown as a positive control. (B) RT-PCR analysis of Sox17 and GATA4 RNA expression. RNA obtained on differentiation days 8 and 10 of wt ES cells, from two different G6pdΔ lines, and from G6pdΔ$^{pG6pd}$ cells.

It is claimed herein a method comprising the inhibition of the PPP pathway for the differentiation of pluripotent cells towards endodermal-type precursors.

Said method comprises:
a) the maintenance in culture of said pluripotent cells;
b) the dissociation of said pluripotent cells and plating thereof on plates that are treated for cell culture, and their in vitro differentiation;
c) the inhibition, before or during said step b) of the pentose phosphate pathway in said pluripotent cells.

In an embodiment, said pluripotent cells are animal or human ES cells. In a further embodiment, said pluripotent cells are animal or human iPS cells. Where said method is applied to human ES cells, such cells are selected among the cell lines of human ES cells approved and available for distribution. Said cell lines are listed in the human NIH ES cells register, which can be referred to on the website http://grants.nih.gov/stem_cells/registry/current.htm In an embodiment, said method comprises the gene inactivation of the PPP pathway in said pluripotent cells.

Said gene inactivation of the PPP pathway is preferably dependent on G6pd gene. In an alternative embodiment, it is dependent on Pdg, the gene coding for the phosphogluconate dehydrogenase enzyme. Said gene inactivation is carried out by means of techniques known to those skilled in the art, and it can be obtained by modifications or genetic mutations that prevent the transcription and/or translation of the gene and/or the functionality of the protein encoded by the same. In an alternative embodiment, the deletion of the above-mentioned genes is also feasible.

In a further embodiment, said method comprises the chemical inhibition of the PPP pathway in said pluripotent cells. Said chemical inhibition is obtained by using molecules which are known for their inhibitory ability against key enzymes of the PPP pathway, such as G6PD and PDG, preferably said inhibitors are selected in the group comprising dehydroepiandrosterone (DHEA) and derivatives thereof, and 6-aminonicotinamide (6AN).

In a preferred embodiment, said inhibitor is DHEA, in concentrations ranging between 50 and 300 μM, preferably about 100 μM. Alternatively, said chemical inhibition is obtained by exposing said cells to 6AN in concentrations ranging between 1 and 100 μM, preferably about 10 μM.

The in vitro differentiation procedure comprises the plating of the dissociated cells onto plates treated for cell culture, preferably gelatine-treated plates, in the presence of a culture medium suitable for neural differentiation. Said medium is completely chemically defined, and it does not contain fetal bovine serum. Said medium is preferably knockout Dulbecco MEM (Minimal Essential Medium) supplemented with about 15% KSR (Knockout Serum Replacement, Invitrogen), 2 mM glutamine, 100 U/ml penicillin/streptomycin, and about 0.1 mM β-mercaptoethanol.

By inhibiting, by one of the described methods, the PPP pathway in pluripotent cells, and by exposing them to a culture medium suitable for neural differentiation, a cell population is obtained in a reproducible and efficient manner, having characteristics that are typical of the endodermal precursors. In particular, pluripotent cells in which the PPP pathway has been genetically or chemically inhibited, express, from the differentiation day 8, GATA 4 (a mesoendodermal marker) and Sox17 (marker of endodermal precursors). On the other hand, the same markers are not expressed in pluripotent cells that are differentiated in parallel and in which the PPP pathway has not been inhibited.

The endodermal precursors obtained by the method described herein are further characterized by the propensity to progress further into the differentiation, until giving rise to a mature endoderm. For example, by proceeding further in the differentiation of the endodermal precursors obtained, the expression of a marker, Pdx1, which is characteristic of the pancreatic precursors, has been observed.

It is a further aspect of the present invention a population of endodermal precursor cells expressing GATA4 and Sox17 that have never been exposed to non-human antigens for use in regenerative therapy. In particular, said cells have never been exposed to fetal bovine serum. In a preferred embodiment, said cells are obtained according to the method described herein.

The following examples have the purpose of illustrating the method claimed herein and characterizing the cell population obtained by exposing pluripotent cells to the method described herein, are not to be construed as limiting the present invention.

Example 1

Differentiation of Wild-Type (Wt) and G6PdΔ Murine Embryonic Stem Cells

Wt murine or with a deletion of the gene coding for G6PD (G6pdΔ) embryonic stem (ES) cells have been differentiated following the method described in Fico et al. (Fico A et al., Stem Cells Dev 2008). Briefly, 48 h before the induction of the differentiation, the ES cells have been plated onto pre-gelatinized plates. On day 0, the cells have been dissociated, thus obtaining a single cell suspension, which have subsequently been plated onto gelatinized plates at a density of 1.500 cells/cm2. During the differentiation process, the culture medium has been changed every other day for the first 6 days, then daily. The culture medium used consists in the medium free from integrated Knockout Serum Replacement (KSR) serum, and contains knockout Dulbecco minimal essential medium, integrated with 15% KSR (Invitrogen), 2 mM glutamine, 100 U/ml penicillin/streptomycin, and 0.1 mM β-mercaptoethanol.

From 6 days of differentiation, the expression profiles of markers of undifferentiated cells and specific markers for the three germ layers have been analyzed by RT-PCR. The expression of Oct4 and Nanog, markers of undifferentiated ES cells, is detectable in both cell lines (FIG. 1A). Furthermore, no difference in the expression profile of Nestin (marker of neuronal precursors), NF-L (marker of neurons), Blbp and GFAP (markers of glial cells), T, and Nkx2.5 has been observed between wt cells and G6pdΔ cells (FIG. 1A). αMHC (a marker specific to cardiomyocytes) is not expressed in both cell lines. Surprisingly, the expression of endodermal markers is never present during the differentiation of wt ES cells, while, from the differentiation day 8, the GATA 4 expression (meso-endodermal marker) and Sox17 (marker of endodermal precursors) expression is observed in G6pdΔ cells (FIG. 1A). The expression of Sox17 in G6pdΔ cells, but not in wt cells is confirmed by the immunofluorescence analysis carried out thereon at 10 differentiation days by using specific anti-Sox17 antibodies. For the immunofluorescence analysis, the cells are fixed in 4% paraformaldehyde/PBS 1X at room temperature for 30 min. After the fixation, 3 washes for 5 minutes have been carried out with PBS1X, and subsequently the samples have been incubated with 10% normal goat serum (Dako Cytomation, Glostrup, Denmark)/0.1% Triton X-100 in PBS1X for 15 minutes at room temperature. Then the cells have been washed 3 times with PBS1X for 5 min., and incubated with the primary antibody of interest in 10% normal got serum/PBS1X at the following dilutions; specifically, anti-Sox17 (1:20, R&D) has been used. After the incubation with the primary antibody, the cells have been washed 3 times in PBS1X, and then incubated with the secondary Texas red-conjugated goat anti-mouse IgG (1:400; Molecular Probes) antibody in 10% normal goat serum/PBS1X for 30 min. at room temperature. Then, samples were washed 4 times in PBS1X and the nuclei stained with DAPI (250 ng/mL, Sigma-Aldrich).

Samples were observed under an inverted microscope (DMIRB, Leica Microsystems, Wetzelar, Del., http://www.leica-microsystems.com), and images were acquired by a DC 350 FX camera (Leica).

Figure 1B:
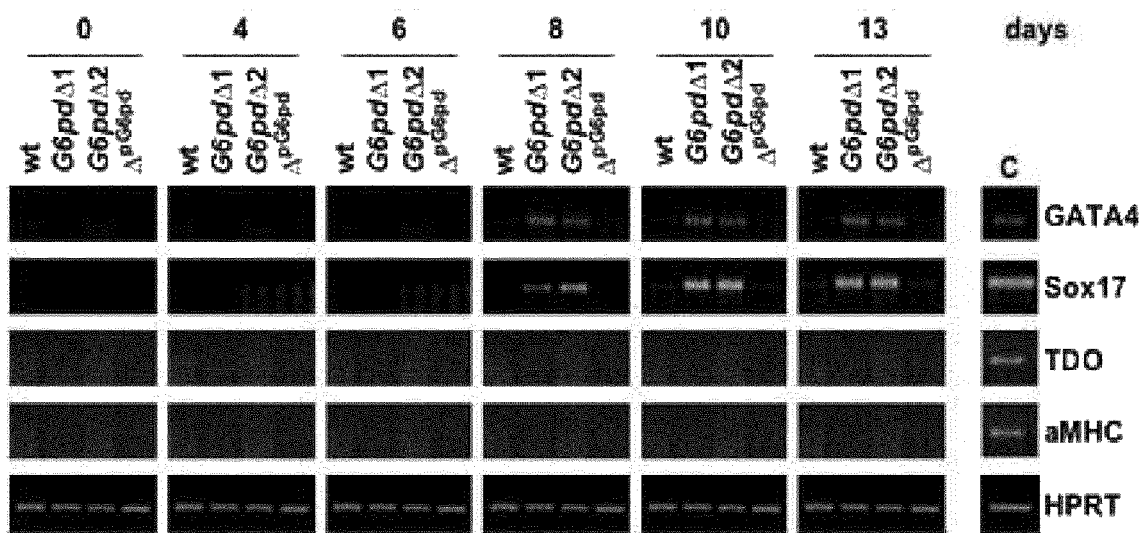

To confirm that the observed expression of specific endodermal markers was dependent on the inactivation of the G6PD gene, and not on any accidentally produced additional anomalies, the same markers were analyzed after the differentiation in two different lines of ES cells, in which the G6PD gene had been deleted, lines G6pdΔ1 and G6pdΔ2, obtaining similar results (FIG. 1B).

Example 2

Differentiation of G6PdΔ$^{pG6pd}$ Murine Embryonic Stem Cells

G6pdΔ$^{pG6pd}$ cells, i.e., G6pdΔ cells transfected with an expression vector containing a puromycin-resistance gene in which the expression of the G6PD gene is under the control of the β-actin promoter, have been used. Consequently, the G6PD expression turns out to be restored. To confirm the role played by G6PD in the endodermal differentiation, during the differentiation of G6pdΔ$^{pG6pd}$ cells, which took place by following the same method used in Example 1, the expression of GATA4 and Sox17 has never been observed (FIG. 1B).

Example 3

Induction of Defined and Extra-Embryonic Endoderm

To date, markers expressed exclusively in the definitive endoderm are not available; however, it has been shown in Borowiak et al. (supra) that the morphology acquired by Sox17-positive cells is capable of discriminating between definitive endodermal cells or extra-embryonic endodermal cells. Sox17+ cells that occur grouped belong to the definitive endoderm, while isolated Sox17+ cells belong to the extra-embryonic endoderm. In fact, the grouped Sox17 cells do not express extra-embryonic endodermal markers. During the differentiation of the G6pdΔ cells, grouped, but also dispersed, Sox17+ cells have been observed. The presence of extra-embryonic GATA4 and Sox7 markers has been confirmed (FIG. 1A) by a RT-PCR analysis, thus leading to the conclusion that during the differentiation of G6pdΔcells definitive and extra-embryonic endodermal cells are induced.

Example 4

Role of Pentose Sugars in Differentiation Towards Endodermal Precursors

Figure 2A:
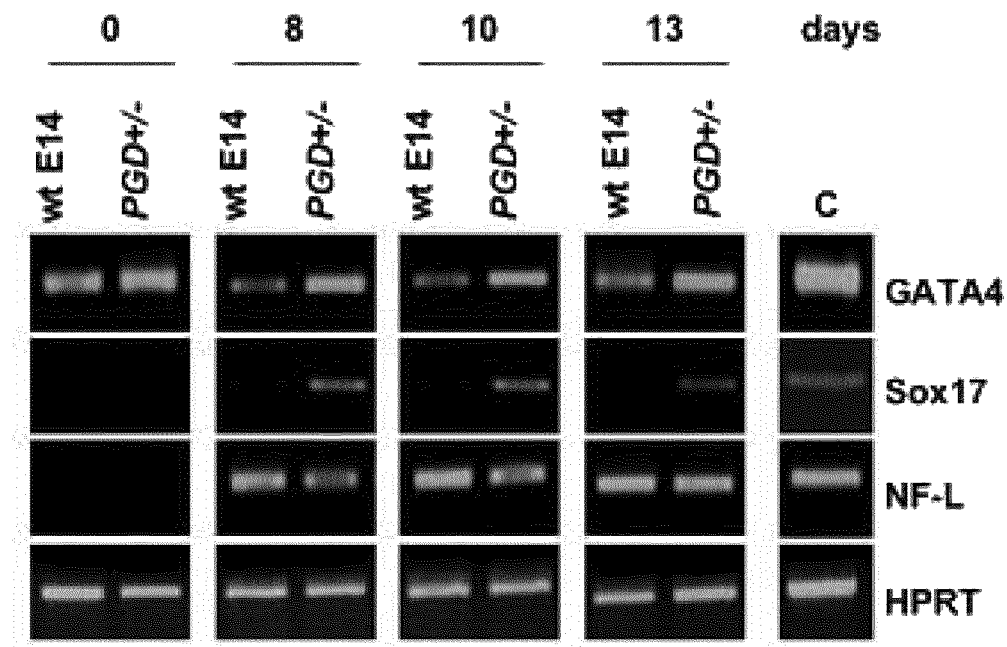
FIG. 2: (A) RT-PCR analysis of the expression of different specific differentiation markers in wt and Pgd+/− cells on neural differentiation days 8 and 10. (B) QRT-PCR analysis of Sox17 expression in wt ES e G6pdΔ cells after 10 neural differentiation days in the presence of D-(−)-ribose.
Figure 2B:
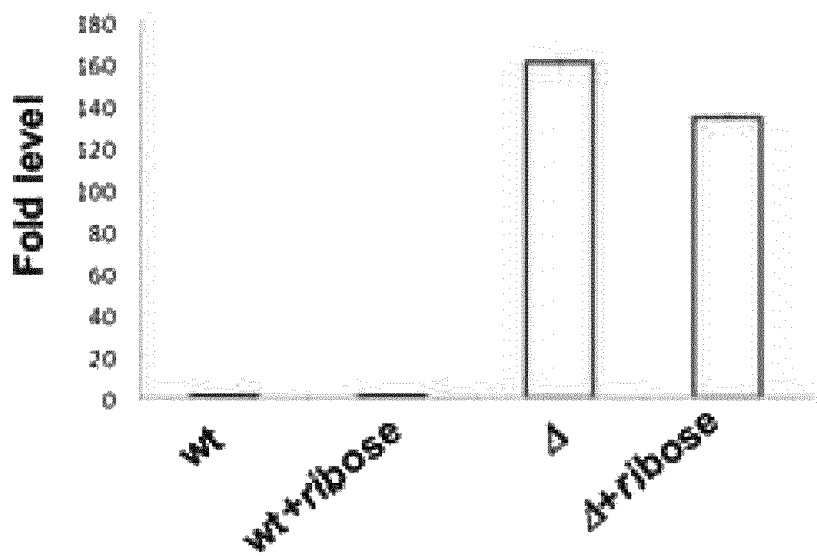

Heterozygous knock-out ES Pdg+/− cells for the phosphogluconate dehydrogenase (PDG) enzyme, the second enzyme present in the PPP, were exposed to the above-described differentiation procedure. These cells have reduced Pdg mRNA levels, and are not sensitive to oxidative stress. As noted before in relation to G6pdΔ cells, Pdg+/− cells are also capable of differentiating towards endodermal cells (FIG. 2A), thus suggesting the importance of a PPP modulation in order to adjust the differentiation towards endoderm. Furthermore, G6pdΔ cells were exposed to the same differentiation procedure, but in the presence of D-(−)-ribose. Despite the addition of D-(−)-ribose does not lead to any variation in the differentiation of wt ES cells, a quantitative (real-time) PCR showed a reduction in Sox17 mRNA levels in G6pdΔ cells (FIG. 2B).

The real-time PCR analysis was carried out with a Biorad CFX 96 Real time System apparatus using a SYBR Green PCR Master Mix (Biorad) and the protocol recommended by the manufacturer. The relative expression of the various genes was normalized by using GAPDH as the gene standard. The used oligos were:

| Gene | forward | reverse |
|------|---------|---------|
| Sox17 | GGAGGGTCACCACTGCTTTA (SEQ ID NO: 1) | AGATGTCTGGAGGTGCTGCT (SEQ ID NO: 2) |
| GATA4 | cactatgggcacagcagctcc (SEQ ID NO: 3) | ttggagctggcctgcgatgtc (SEQ ID NO: 4) |
| GAPDH | TCTTCTGGGTGGCAGTGATG (SEQ ID NO: 5) | TGCACCACCAACTGCTTAGC (SEQ ID NO: 6) |

Example 5

PPP Chemical Inhibition in Wt ES Cells

A known chemical inhibitor of G6PD is DHEA, while a known chemical inhibitor of PDG is AN. Subsequently, their effect on the differentiation of wt ES cells was tested. The immunofluorescence analysis, which was carried out according to the method described in Example 1, revealed that both substances are capable of inducing the differentiation of wt ES cells towards Sox 17+ cells.

Example 6

Differentiation of ES Cells Towards Pancreatic Precursors

G6pdΔ cells on differentiation day 8, that are already expressing Sox17, are exposed to Indolactam V, an inducer of the differentiation of endoderm precursors towards pancreatic precursors. After a 4 day exposure, the expression of Pdx1, a marker of pancreatic precursors, is observed therein. In particular, by a Real Time PCR carried out by using the above-described method and equipment, an increase of about 2.5 times in the Pdx1 expression levels is observed in Indolactam V-exposed cells compared to control cells. The oligos used for the Real Time PCR analysis are as follows:

| Gene | forward | reverse |
|------|---------|---------|
| Pdx1 | TCACGCGTGGAAAGGCCAGT (SEQ ID NO: 7) | GTGTAGGCAGTACGGGTCCT (SEQ ID NO: 8) |
| GATA4 | cactatgggcacagcagctcc (SEQ ID NO: 9) | ttggagctggcctgcgatgtc (SEQ ID NO: 10) |
| GAPDH | TCTTCTGGGTGGCAGTGATG (SEQ ID NO: 11) | TGCACCACCAACTGCTTAGC (SEQ ID NO: 12) |

The invention claimed is:

1. A method for obtaining endodermal-type precursors from pluripotent cells, comprising:
   a) maintaining in culture said pluripotent cells;
   b) dissociating said pluripotent cells and plating said dissociated pluripotent cells onto gelatin-coated plates for cell culture and in vitro differentiating the pluripotent cells in the presence of a serum-free neural differentiation culture medium;
   c) inhibiting, either before or during said step b), expression or activity of an enzyme in the oxidase phase of the pentose phosphate pathway (PPP) at an effective level to inhibit the production of ribulose-5-phosphate in said pluripotent cells.

2. The method according to claim 1, wherein said pluripotent cells are animal or human embryonic stem cells, or they are animal or human induced pluripotent stem (iPS) cells.

3. The method according to claim 1, wherein said inhibition of expression or activity of an enzyme in the oxidase phase of the PPP at an effective level to inhibit the production of ribulose-5-phosphate occurs by gene inactivation of the enzyme in said pluripotent cells.

4. The method according to claim 3, wherein said gene inactivation comprises inactivation of a glucose-6-phosphate dehydrogenase (G6pd) gene or inactivation of a phosphogluconate dehydrogenase (Pdg) gene.

5. The method according to claim 3, wherein said gene inactivation is obtained by genetic modifications or mutations that inhibit transcription and/or translation and/or functionality of the encoded enzyme in the oxidative phase of the PPP, or by gene deletion.

6. The method according to claim 1, wherein said inhibition of expression or activity of an enzyme in the oxidase phase of the PPP at an effective level to inhibit the production of ribulose-5-phosphate occurs by chemical inhibition of the enzyme in said pluripotent cells.

7. The method according to claim 6, wherein said chemical inhibition is obtained by using an inhibitor of glucose-6-phosphate dehydrogenase (G6PD) and/or an inhibitor of phosphogluconate dehydrogenase (PDG), said inhibitors are selected from the group consisting of: dehydroepiandrosterone (DHEA), derivatives of DHEA, and 6-aminonicotinamide (6AN).

8. The method according to claim 1, wherein said neural differentiation culture medium comprises knockout Dulbecco MEM (Minimal Essential Medium), about 15% KSR (Knockout Serum Replacement), about 2 mM glutamine, about 100 U/ml penicillin/streptomycin, and about 0.1 mM β-mercaptoethanol.

* * * * *